United States Patent
Yasumoto et al.

(10) Patent No.: US 6,916,655 B2
(45) Date of Patent: Jul. 12, 2005

(54) CULTURED SKIN AND METHOD OF MANUFACTURING THE SAME

(75) Inventors: Shigeru Yasumoto, Kanazawa-ken (JP); Masakatsu Takeuchi, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/300,906

(22) Filed: Nov. 21, 2002

(65) Prior Publication Data

US 2003/0096409 A1 May 22, 2003

(30) Foreign Application Priority Data

Nov. 22, 2001 (JP) .................................. 2001-356945

(51) Int. Cl.⁷ .............................. C12N 5/08; C12N 5/00
(52) U.S. Cl. ...................... 435/371; 435/366; 435/383; 435/404
(58) Field of Search ................................ 435/371, 366, 435/383, 404, 1.1, 395; 623/15.12, 901

(56) References Cited

U.S. PATENT DOCUMENTS

| | | | |
|---|---|---|---|
| 4,883,487 A | | 11/1989 | Yoshizato et al. ............. 623/15 |
| 5,712,163 A | * | 1/1998 | Parenteau et al. .......... 435/405 |

FOREIGN PATENT DOCUMENTS

| | | |
|---|---|---|
| DE | 36 08 329 A1 | 9/1987 |
| DE | 101 09 136 A1 | 9/2002 |
| DE | 101 09 136 A 1 | 9/2002 |
| EP | 0 012 774 A1 | 7/1980 |
| EP | 0 084 157 A2 | 7/1983 |
| FR | 2 563 727 A | 11/1985 |
| FR | 2 563 727 A1 | 11/1985 |
| GB | 2 365 443 A | 2/2002 |
| JP | 4-332561 A | 11/1992 |
| JP | 5-184662 A | 7/1993 |
| JP | 2000-125855 A | 5/2000 |
| WO | 96/12510 A1 | 5/1996 |
| WO | 00/30695 A1 | 6/2000 |

OTHER PUBLICATIONS

Pelletier et al. Epithelial cells primary cultures and fibroblasts long–term cultures from human umbilical cord ultra– structural and immunocytochemical characterization. C. R. Soc. Biol. 1986, 180, pp. 447–459.*

Black, Annie F., et al.; "In vitro reconstruction of a human capillary–like network in a tissue–engineered skin equivalent"; The FASEB Journal; vol. 12, No. 13, pp. 1331–1340; Oct. 1998.

Black, A.F. et al.; "In vitro Reconstruction of a Human Capillary–like Network in a Tissue–engineered Skin Equivalent"; The FASEB Journal; vol. 12, pp. 1331–1340; 1998.

Mizoguchi, M. et al.; "Reconstruction of a Human Skin Equivalent using Epithelial Cells Derived from Umbilical Cord"; The Journal of Investigative Dermatology; vol. 117, p. 422; 2001; abstract.

Mizoguchi, M. et al.; "Expression of Cytokeratins and Cornified Cell Envelope–Associated Proteins in Umbilical Cord Epithelium: a Comparative Study of the Umbilical Cord, Amniotic Epithelia and Fetal Skin"; The Journal of Investigative Dermatology; vol;. 115, pp. 133–134; 2000.

Gu, J. et al.; "Detection of Endothelin–like Immunoreactivity in Epithelium and Fibroblasts of the Human Umbilical Cord"; Tissue and Cell; vol. 23, pp. 437–444; 1991.

* cited by examiner

Primary Examiner—Vera Afremova
(74) Attorney, Agent, or Firm—Kubovcik & Kubovcik

(57) ABSTRACT

A cultured skin and a grafting cultured skin sheet are provided, each of which is a cultured reconstructive skin with a high take rate using cells collectable from cells originated from tissue included in an umbilical cord such as tissue included in an umbilical cord originated from a human fetus. The grafting cultured skin stratified sheet is prepared by placing an epithelium sheet on the top surface of a cultured dermis. The cultured dermis includes as components a cultured skin containing cells originated from a tissue included in an umbilical cord, such as umbilical cells, more concretely, umbilical fibroblast cells, being separated and cultured, preferably in a collagen nonwoven fabric. On the other hand, the epithelium sheet is prepared by culturing and stratifying the umbilical cord epithelium cells.

1 Claim, 3 Drawing Sheets

CULTURED SKIN AND METHOD OF MANUFACTURING THE SAME

TECHNICAL FIELD OF THE INVENTION

The present invention relates to a cultured skin including cells originated from tissue included in an umbilical cord, such as umbilical cells, placental cells, and velamen cells. More specifically, the present invention relates to an artificial cultured skin to be used for skin grafting and cell therapy for various kinds of tissue reconstruction or regenerative medicine.

BACKGROUND OF THE INVENTION

A skin is provided as a boundary between a living body and an external environment and has functions of maintaining a liquid in the living body, reducing friction in water, keeping body temperature constant, and protecting the inside of the living body from physical damages.

The skin of a vertebrate animal consists of a connective tissue layer generally regarded as dermis originated from the mesoderm and epidermis stratified thereon originated from the ectoderm.

Cultured skin is constructed from a part of a skin structure by in vitro culture of epithelium cells (i.e., epithelial cells) and fibroblasts collected from a piece of healthy skin (a piece of epithelium). It is also referred to as autologous cultured skin when cells collected from a piece of a patient's own healthy skin (a piece of epithelium) are used or an allogeneic cultured skin when cells collected from a piece of healthy skin (a piece of epithelium) of another patient are used.

The cultured skins can be applied in medical treatments for severe burns, diabetic ulcers of lower limbs, and venous ulcerative inflammation, treatment of scars after plastic surgery, and so on. The cultured skins are not only effective in simply covering a wounded surface but are also effective in secreting or supplying growth factors or the like required for wound healing.

Currently, as sources for supplying human functional epithelium cells, cultured skins using constructive materials prepared from neonatal and adult penis foreskins, epithelium cells originated from oral mucosa, fibroblasts originated from skins, and matrices including collagen, fibrin, heparin, silicon, and so on have been reported (JP-A 246371/1987, JP-A 332561/1992, JP-A 125855/2000, JP-A 157624/2000, Japanese Patent No. 3105308, and "Nikkei Bio Nenkan 2000")

However, epithelium cells of the tissues provided as origins of the above cells are those in which cell differentiation and aging have progressed, so that their cell division lifetime may be short and their capacity for differential plasticity may be small. Furthermore, there are many unsolved problems in the art. For instance, there are variations in the collections of cell populations, instability of healthy tissues, dimensions of tissues, and so on. Ethical problems are caused in offering of an excess normal tissue obtained at the time of surgical operations, and so on.

SUMMARY OF THE INVENTION

The present inventors have made dedicated efforts to provide a cultured reconstructive skin with a high successful grafting rate using cells collectable from tissues included in an umbilical cord originated from a human fetus, finally completing the present invention.

That is, the present invention relates to:
(1) a cultured skin comprising cells originated from tissue included in an umbilical cord;
(2) a cultured skin as described above in item 1, wherein the cells originated from the tissue included in the umbilical cord are umbilical cord cells;
(3) a cultured skin comprising umbilical cells as components of an epithelium layer (i.e., epithelial layer) or a dermal layer;
(4) a cultured skin as described above in item 2 or 3, wherein the umbilical cells are umbilical cord epithelium cells or umbilical cord myofibroblasts;
(5) a cultured skin as described above in item 2 or 3, wherein the umbilical cord cells are umbilical epithelium cells separated from umbilical cord tissue and cultured or umbilical cord myofibroblasts separated from umbilical cord tissue and cultured;
(6) a grafting cultured skin stratified sheet comprising umbilical cord epithelium cells separated from cells originated from tissue included in an umbilical cord and cultured, which are further cultured and stratified on a surface of cultured dermis containing umbilical cord fibroblasts which were separated from cells originated from tissue included in an umbilical cord and cultured;
(7) an epithelium sheet comprising umbilical cord epithelium cells separated from cells originated from tissue included in an umbilical cord and cultured, which are cultured and stratified;
(8) a cultured dermis comprising umbilical fibroblasts separated from cells originated from tissue included in an umbilical cord and cultured as components;
(9) a method of separating umbilical cord epithelium cells, which comprises: [1] immersing tissue included in an umbilical cord in a proteolytic enzyme to loosen bonding of the tissue included in the umbilical cord; [2] peeling the tissue included in the umbilical cord by physical means; and [3] separating the peeled tissue into cells using the proteolytic enzyme;
(10) a separation method as described above in item 9, wherein the proteolytic enzyme is an enzyme selected from the group consisting of dispase, trypsin, and collagenase.
(11) a method of culturing umbilical cord epithelium cells, characterized by culturing the umbilical cord epithelium cells separated from cells originated from tissue included in an umbilical cord in a medium;
(12) a culture method as described above in item 11, wherein the medium includes a human epithelium cell growth medium;
(13) a culture method as described above in item 11, wherein the culture is performed in the medium contained in a culture vessel coated with an extracellular adhesion material;
(14) a method as described above in item 13, wherein the extracellular adhesion material is selected from the group consisting of collagen, laminin, elastin, proteoglycan, tenascin, and fibronectin.
(15) a method of manufacturing a grafting cultured skin stratified sheet, characterized in that umbilical cord epithelium cells separated from cells originated from tissue included in an umbilical cord and cultured are inoculated on a top surface of cultured dermis containing as components umbilical fibroblasts separated from cells originated from tissue included in an umbilical cord and cultured and are then cultured and stratified; and
(16) a method of manufacturing a grafting cultured skin stratified sheet, characterized in that umbilical cord epithelium cells separated from cells originated from tissue included in an umbilical cord and cultured are inoculated on a top surface of a dermal layer constructed of collagen gel and umbilical fibroblasts and are then cultured and stratified.

A: MCDB153-1/4(0% cx-FCS) medium

B: Keratinocyte-SFM medium (GIBCO)

C: Defined Keratinocyte-SFM medium (GIBCO)

In the figure, plots show the passage days of the culture.

Figure 2:
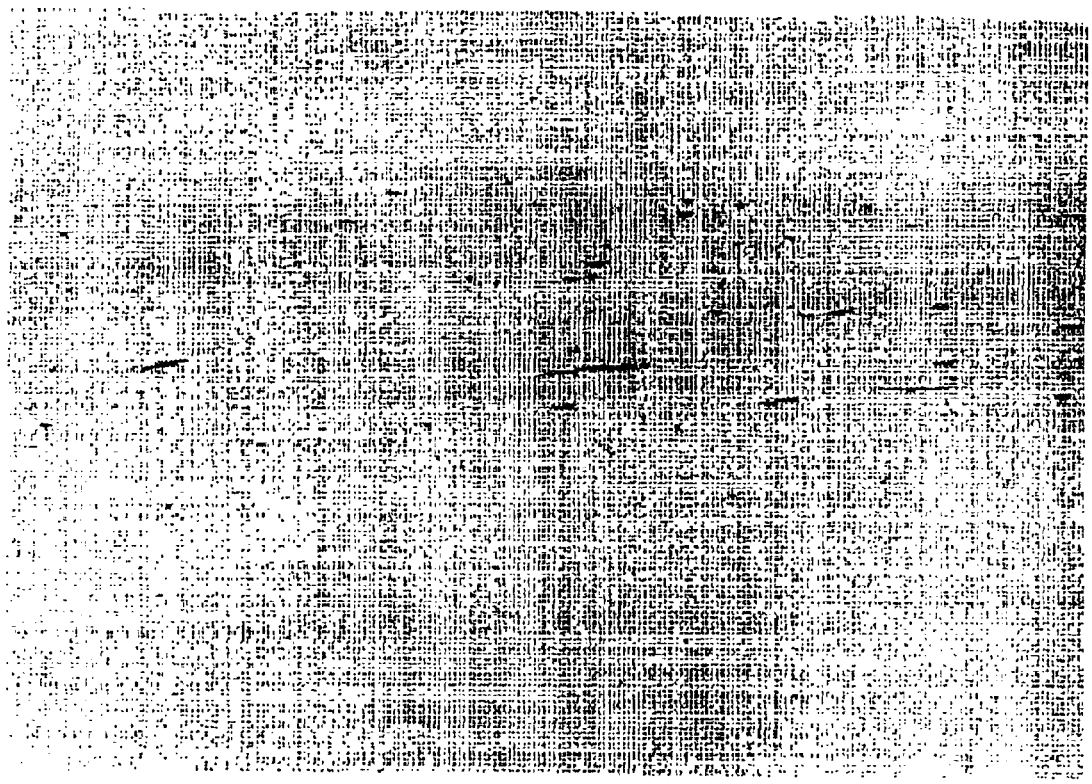

FIG. 2 is a cross sectional view of cultured dermis.

A cross sectional HE stain of the cultured dermal tissue, where each of umbilical myofibroblasts being observed is in the shape of a narrow piece, a particle, or the like is shown.

Figure 3:

FIG. 3 is a cross sectional view of cultured skin.

A cross sectional HE stain of the cultured skin tissue, where the epithelium layer in which several layers thereof are stratified on the cultured dermis is observed.

DETAILED DESCRIPTION OF THE INVENTION

In the present invention, the term "cells originated from tissue included in an umbilical cord" refers to, for example, umbilical cells, placenta cells, velamen cells, and so on. The umbilical cells are constitutive cells of an umbilical cord. The umbilical cord is a human fetal appendage and becomes unnecessary after birth. However, it can be provided as a successive source of supplying fetal cells that retain potential self-regenerative activities and capacity for differential plasticity. The placenta cells are those of an elliptically squamous organ comprising fetal chorion frondosum and maternal decidua basalis. The fetal side of the organ is covered with the amnion. The velamen cells are those of components of a membrane that enwraps an embryo or the like in a uterus, which are formed from decidua, chorion, and amnion in that order from the outer layer. The amnion is a semi-translucent thin film that covers the fetal side of the placenta and the inside of the velamen. An epithelium of the amnion indicates a shift to the surface of umbilical cord, i.e., an epithelium tissue on the umbilical cord and fetal skin portion. The amnion consists of five layers including a mono layer of an epithelium cell layer and a fibroblast layer, while the chorion consists of four layers including a fibroblast layer.

Umbilical cells to be used in the present invention include umbilical epithelium cells and umbilical myofibroblasts separated from umbilical tissue.

In general, umbilical tissue (prenatal fetal tissue) is comprised of an umbilical epithelium (including an external layer), Wharton's jelly that involves umbilical myofibroblasts, two umbilical arteries, and one umbilical vein. In the body, the umbilical tissue is in a growth process, and also the umbilical epithelium is a part of epithelial tissue of a body surface. Therefore, it is a tissue that contains many regenerative epithelial stem cells without a progress in aging, as distinct from adult skin. This can be supported by a high telomerase activity and a long telomere length. The division lifetime (aging) of the cell can be delayed by such telomerase activity and allows the preparation of graft skin with a long term take.

Furthermore, the cellular aging delay effect can be easily exerted by the introduction of a cell-immortalizing gene.

Also, it is known that such an effect of the above cell where a cell-immortalizing gene is introduced is extremely higher than that of adult skin cells (up to several hundred times). From this fact, it is clear that the potential division abilities of umbilical epithelium cells are extremely high.

However, the introduction of an immortalizing gene involves a modification of cells. Thus, there is no restraint on the preparation of cultured skin sheet using immortalizing umbilical epithelium with respect to a combination with an operation of removing the transgene from the cell. Further, implementation thereof does not restrict application of using an adeno-cre-Lox system known in the art.

Furthermore, the surface layer of the umbilical cord is connected to the surface skin of a fetus, so that there is a possibility that the cells included in the umbilical cord have the same or more excellent regenerative abilities, compared with those of adult skin cells.

Moreover, as those cells are originated from a fetus, there are further advantages in that the lifetime of cell division can be longer than others and a high potential growth ability can be attained.

The umbilical epithelium cells to be used in the present invention are those grown by separating columnar epithelium cells in about one to three layers of the epithelium layers that cover the umbilical outermost layer, followed by culture.

The method of separating the umbilical epithelium cells includes the following steps of:

(1) immersing a tissue included in an umbilical cord in a proteolytic enzyme to loosen the binding of the tissue included in the umbilical cord;

(2) peeling the tissue included in the umbilical cord by physical means; and (3) separating the peeled tissue into cells by the proteolytic enzyme.

Preferably, for obtaining the umbilical epithelium cells of the present invention, a piece of epithelium tissue is separated by treating the tissue included in the umbilical cord such as an umbilical tissue with a proteolytic enzyme or the like and the resultant tissue is further broken into cells by treating with a solution of trypsin-EDTA or the like. The proteolytic enzyme may be dispase, trypsin, collagenase, or the like, which is an enzyme capable of degrading fibronectin and collagen type I or IV. In the step of physically peeling the umbilical tissue (a piece epithelium tissue), instruments such as a scalpel, a pair of tweezers, and a brush are used.

According to the present invention, the medium for the culture of umbilical epithelium cells in the present invention is not specifically limited. However, one of media including those used for epithelium cells other than umbilical epithelium cells or fibroblasts may be used. Such media include those for animal cells, such as MCDB153 (Sigma), keratinocyte-SFM (GIBCO), Defined keratinocyte-SFM (GIBCO), EpiLife-KG2 (Kurabo), HuMedia-KG2 (Kurabo), HuMedia-KB2 (Kurabo), DMEM (Sigma), RPMI1640 (GIBCO), Medium 106S (Kurabo), and so on. Among them, it is preferable to prepare and use a medium (MCDB153-1/4) as a mixture of the MCDB153 medium (including supplements) and the DMEM medium (including 0–10% FBS) at a volume ratio of 4:1.

The culture vessels to be used in the present invention include culture dishes, culture flasks, membranes, cover glasses, and so on. Typically, they are made of polystyrene, glass, polypropylene, TC-treated polycarbonate, blended cellulose ester, hydrophilic-treated PTFE (IWAKI, NUNC, CORNING, FALCON), or the like. In addition, preferably, each of their surfaces may be coated with an extracellular adhesive material. The extracellular adhesive material may include one selected from the group consisting of collagen, laminin, elastin, proteoglycan, tenascin, and fibronectin. The epithelium cells maintain contact with the connective tissue under them through a basal lamina. Therefore, it is preferable to use a culture vessel coated with collagen type I or IV, which is a component of the basal lamina.

The culture conditions to be used in the present invention are preferably of about 37° C. and 100% humidity in the presence of 5% carbon dioxide. However, the present invention is not limited to these conditions.

The umbilical myofibroblasts to be used in the present invention are those grown by separating myofibroblasts included in Wharton's jelly in the umbilical cord, followed by the culture thereof.

The umbilical fibroblasts may be prepared by a method in which fibroblasts in the tissue included in the umbilical cord are separated and cultured to allow the growth thereof.

The method of separating the umbilical fibroblasts may be one in which umbilical fibroblasts are separated from the tissue included in the umbilical cord, such as an umbilical tissue by means of an explant culture method.

The explant culture method is one for culturing a small piece of tissue taken from the living body, allowing the collection of cells liberated and grown from the tissue.

The umbilical myofibroblasts separated from the umbilical tissue can be cultured in the medium in a culture vessel. More concretely, the umbilical myofibroblasts may be preferably separated and cultured using an explant culture method after separating the umbilical epithelium cells and removing blood vessels within the umbilical cord from the umbilical tissue. Concretely, for example, the umbilical tissue is cut out into small tissues of about 1 to 5 mm squares using a scalpel or the like, followed by leaving them at rest in a culture vessel containing the DMEM medium (including 10% of FBS) for 5 to 10 days. Then, the umbilical myofibroblasts being migrated and divided and grown from the periphery of the tissue are separated using a solution such as trypsin-EDTA or the like, followed by the culture of the thus-obtained cells in the DMEM medium (including 10% of FBS) for 5 to 30 days.

The medium to be used for umbilical myofibroblasts of the present invention is snot specifically limited. However, for example, DMEM (Sigma), RPMI1640 (GIBCO), and Medium106S (Krabo) can be exemplified. Among them, especially, the DMEM medium (including 10% FBS) is preferable.

The culture vessels to be used in the present invention include culture dishes, culture flasks, cover glasses, and so on. The culture conditions to be used in the present invention are preferably of about 37° C. and 100% humidity in the presence of 5% carbon dioxide. However, the present invention is not limited to these conditions.

The cultured skin to be prepared in the present invention is a two-layered cultured skin prepared using a skin of the living body as a model, where the skin includes an epidermal layer and dermal layer and umbilical cells are included as components of the epidermal and dermal layers.

Among the umbilical cells, preferably, umbilical epithelium cells may be in the epidermal layer, while umbilical myofibroblasts may be in the dermal layer. The epidermal layer can be prepared by stratifying 4 to 10 layers of the umbilical epithelium cells. On the other hand, the dermal layer can be prepared using the umbilical myofibroblasts as carriers, preferably together with an extracellular matrix such as collagen.

The epithelium sheet to be prepared in the present invention is a cultured epithelium prepared using the epithelium layer of the skin of the living body as a model. Preferably, it may be prepared by stratifying 4 to 10 layers of the umbilical epithelium cells.

The cultured dermis to be prepared in the present invention is one preferably prepared using the dermal layer of the skin of the living body as a model, while the umbilical myofibroblasts are used as carriers, preferably together with an extracellular matrix such as collagen. In a specific testing method, when the fibroblasts are only grafted in an in vitro environment, such fibroblasts are multiplied so that collagen can be produced. As a result, a dermis-like tissue is formed. Typically, in the in vitro environment, the dermal layer cannot be formed using the fibroblasts only.

As the extracellular matrices, collagen non-woven fabric, collagen gel, collagen sponge, collagen sheet, and so on can be exemplified.

Instead of these carriers, alternatively, bio-absorbable substrates (glycosaminoglycan, glycolic acid, lactic acid, chitin, polyglactin, chondroitin sulfate, and fibrinogen) and so on may be used.

The method of manufacturing cultured dermis using the carrier may be one in which fibroblasts are inoculated in the carrier or inoculated on the carrier to allow a successful grafting, followed by culturing for 1 to 4 weeks. In the case of gel carrier, the carrier in a liquid form is mixed with fibroblasts and is then gelated and cultured for 1 to 4 weeks to prepare cultured dermis that includes fibroblasts in the gel.

Preferably, the cultured dermis is of 0.5 to 3 mm in thickness and is provided in the shape of a smooth sheet.

A grafting cultured skin stratified sheet of the present invention is prepared by placing an epithelium sheet on the surface is of a cultured dermis which includes umbilical fibroblasts. That is, a grafting cultured skin stratified sheet of the present invention is prepared by a process that separated and cultured umbilical epithelium cells are further cultured and stratified on the surface of a cultured dermis including separated and cultured umbilical fibroblasts as components thereof.

Alternatively, a grafting cultured skin stratified sheet of the present invention is prepared by placing an epithelium sheet on the surface of a dermal layer consisting of collagen gel prepared from a collagen solution and umbilical fibroblasts. That is, a grafting cultured skin stratified sheet of the present invention is prepared by a process that separated and cultured umbilical epithelium cells are further cultured and stratified, on the surface of a dermal layer consisting of collagen gel prepared from a collagen solution and umbilical fibroblasts.

In the case that the separated and cultured umbilical epithelium cells are cultured and stratified on the surface of the cultured dermis or the dermal layer, separated umbilical epithelium cells or umbilical epithelium cells previously cultured once are inoculated and cultured on the surface of the cultured dermis or the dermal layer, followed by further stratifying. This kind of stratified structure can be attained by continuing the culture under conditions including the addition of an epithelium cell differentiation factor and air exposure of the epithelium layer.

Generally, stratifying includes the steps of inoculating umbilical cord epithelium (epithelial) cells on the dermal layer, culturing for about 4 to 10 days, preferably at 37° C. in the presence of 5% $CO_2$, and exposure of the epithelium (epithelial) layer to air.

In the grafting cultured skin stratified sheet, the dermal layer has a thickness of 0.5 to 3 mm in general, the number of epithelium layers is 4 to 10 with a thickness of 0.1 to 1 mm in general.

The dermal layer and the epithelium layer may further include vascular endothelial cells, nerve cells, hematopoietic stem cells, blood vessel inducer, epithelium cell differentiation factors, epithelium cell growth factors, and fibroblast growth factors.

The cultured skin of the present invention has a high potential division ability and a comparatively low antigenicity, and is mainly constructed of cells of fetal origin umbilical tissue, which can be successively supplied, so that it can be applied in medical treatments on diabetic leg ulcers, severe burns, and so on.

EXAMPLES

Next, the present invention will be described in more detail with examples. Unless otherwise specified, % indicates % by weight.

Example 1

Separation and Culture of Umbilical Epithelium Cells

An umbilical cord (30–60 cm in length, 9–15 mm in diameter) removed after birth was sufficiently washed three times with HBSS (Hanks' balanced salt solution) or PBS (Phosphate-Buffered Saline solution) to remove adherent blood. Then, both ends of the umbilical cord were tied with strings, respectively, followed by dipping the umbilical cord into a solution prepared by diluting a proteolytic enzyme "dispase"(manufactured by BECTON DICKINSON) with a medium (MCDB153-1/4 medium) having the following composition such that the concentration of the enzyme becomes 20% in the solution. In this case, the umbilical cord was hung by strings and was then dipped into the solution, while both ends (2 cm each) of the umbilical cord were not dipped in the solution, followed by leaving the umbilical cord as it is for 25 to 50 hours at 4° C.

Medium: MCDB153-1/4 Medium (a medium prepared by mixing MCDB153 medium and DMEM (incl., 0–10% FBS) medium together at a blending ratio of 4:1)

The followings are additives in the MCDB153 medium (SIGMA).

| | | |
|---|---|---|
| Epidermal growth factor | Final Concentration | 5 ng/ml |
| Insulin | Final Concentration | 5 µg/ml |
| Transferrin | Final Concentration | 10 µg/ml |
| Hydrocortisone | Final Concentration | 0.2 µM |
| Ethanol amine | Final Concentration | 0.5 µM |
| Phosphoethanolamine | Final Concentration | 0.5 µM |
| Hypophysis extract | Final Concentration | 6.25 µg/ml |
| Dialyzed bovine fetal serum (cx-FCS) | Final Concentration | 0–0.5% |

The following is an additive in the DMEM(SIGMA) medium.

Bovine Fetal Serum (FCS) Final Concentration 0–10%

The dipped umbilical cord was pulled out and was then subjected to the removal of a piece of umbilical epithelium of about 1 mm square in the above MCDB153-1/4 medium using a scalpel, a pair of tweezers, and a brush. Then, the suspension including the piece of the umbilical epithelium was centrifuged to collect only the piece of the epithelium. Subsequently, it was dipped in a solution of 0.1% trypsin and 0.1 mM EDTA for about 10 minutes and was then passed through a mesh (70 µm pore size) to isolate umbilical epithelium cells. After centrifugation, umbilical epithelium cells (about $10^6$ cells) were collected.

The collected umbilical epithelium cells were suspended in the above MCDB153-1/4 medium and were then inoculated in a culture vessel (i.e., a culture dish coated with collagen type IV), followed by placing the culture vessel in an incubator to culture at 37° C. in the presence of 5% $CO_2$.

80% of the umbilical epithelium cells were successfully grafted on the culture vessel and the growth thereof was initiated from the second day.

Example 2

Separation and Culture of Umbilical Myofibroblasts

In Example 1, after separating the umbilical epithelium cells, blood vessels were removed from the remaining umbilical tissue using a scalpel and a pair of tweezers. Then, the umbilical tissue after the removal of blood vessels was cut into pieces of about 5 mm square using a scalpel and a pair of tweezers. Small pieces were rested in the culture dish, while the DMEM medium (incl. 10% FCS) was poured into the culture dish such that one surface of the small piece was dipped in the medium.

After one week past, it was observed that umbilical myofibroblasts were generated around the tissue piece, followed by the addition of about 5 ml of the DMEM medium (incl. 10% FCS) such that the umbilical tissue was sufficiently submerged.

After that, the sufficient growth of umbilical myofibroblasts was allowed and then the umbilical tissue was removed. Consequently, umbilical myofibroblasts (about $10^6$ cells) were collected using a solution of 0.1% trypsin and 0.1 mM EDTA. Subsequently, the cells were suspended in the DMEM medium (incl. 10% FCS) and then inoculated in a new culture dish, followed by culturing in an incubator at 37° C. in the presence of 5% $CO_2$.

In the culture vessel, substantially all of the umbilical myofibroblasts was successfully grafted on the culture vessel and the growth thereof was initiated from the second day.

Example 3

Proliferation of Separated and Cultured Umbilical Epithelium Cells

Umbilical epithelium cells separated in the same way as that of Example 1 were cultured using the following three kinds of media (A, B, C), respectively.

MCDB153-1/4(0% cx-FCS, 0% FCS) medium . . . (A)
Keratinocyte-SFM medium (GIBCO) . . . (B)
Defined Keratinocyte-SFM medium (GIBCO) . . . (C)

A subculture of the umbilical epithelium cells was prepared by collecting the cells using a solution of 0.1% trypsin and 0.1 mM EDTA in a state where the cells had became sub-confluent. The number of cells was counted, followed by inoculating the cells into a culture vessel with a volume three times higher than that of the prior vessel (the volume is the same as in Example 1).

Figure 1:
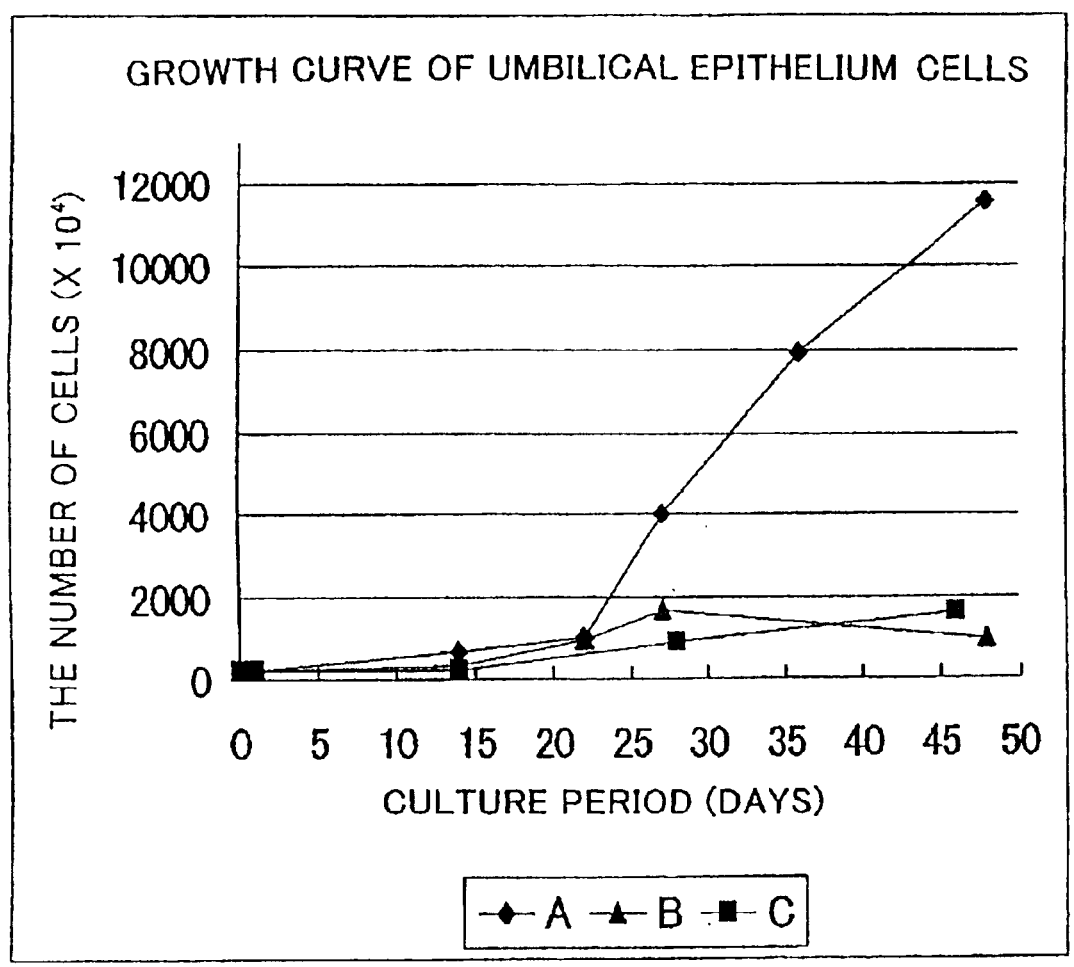
FIG. 1 shows a growth curve of umbilical epithelium cells.

The growth curve of the resultant cells is shown in FIG. 1.

Example 4

Induction of Differentiation of Separated and Cultured Umbilical Epithelium Cells An enzyme labelled antibody (immunoperoxidase) was used for immunostaining of Involucrin or Cytokeratin 14 in the umbilical epithelium cells. Primary antibodies used were follows.

Monoclonal Anti-Involucrin clone SY5 (SIGMA)

Keratin 14 clone RCK107 (SANBIO)

The expression of Involucrin known as a marker of stratum corneum epidermis was observed in the umbilical epithelium layer. In addition, it was also observed in the umbilical epithelium cells in culture.

The expression of Cytokeratin 14 as a marker of epithelial basal layer was also observed in the umbilical epithelium cells in culture.

Example 5

Potential Division Ability (Telomere and Telomerase) of Separated and Cultured Umbilical Epithelium Cells Telomere is a unique structure found in the distal end of a chromosome of the eucaryote and the length of telomere length shortens every cell division. On the other hand, telomerase is an enzyme for synthesis of a telomere repetitive sequence. In a cell having a telomerase activity, the shortening of the telomere sequence caused by every DNA replication is compensated for by the telomerase. Thus, the telomere sequence is stable. From conventional studies, telomere length is regarded as a cell division clock that measures the degree of cellular aging.

The telomerase activities of the umbilical epithelium cells were measured using a TRAP (Telomeric Repeat Amplification Protocol) method, which is a method of detecting the telomerase activity using a high-sensitive and efficient PCR method.

The length of telomere with respect to the umbilical epithelium cells was measured using a Southern blot method which detects a specific gene or DNA fragment on a filter.

As a result, the telomere length of the human skin epithelium cell was 8 to 10 (kbp), while the telomere length of the human umbilical epithelium cell was about 13 (kbp), which was substantially larger than the former. From these results, it becomes evident that the division lifetime of the human umbilical epithelium cell is substantially longer than that of the human skin epithelium cells.

In addition, the telomerase activities were also detected in the umbilical epithelium cells, so that the shortening of the telomere length at the time of cell division can be compensated for, suggesting the presence of a cell having a longer divisional lifetime.

Example 6

Immortalization Sensitivity of Separated and Cultured Umbilical Epithelium Cells The induction of Large-T antigen gene of SV40 was performed using a lipofection method at the time of active proliferation of cells after 2–5 days in primary culture of the umbilical epithelium cells to immortalize the umbilical epithelium cells.

After the gene induction, the long term proliferation ability of 30 passages (about 10 months) or more can be confirmed.

Example 7

Preparation of Cultured Dermis using Umbilical Myofibroblasts

Preparation of a Gel-Adjusting Solution

| | |
|---|---|
| Double-concentrated MCDB153 medium (2 × MCDB) | 16 ml |
| Double-concentrated DMEM medium (2 × DMEM) | 4 ml |
| Bovine fetal serum (FCS) | 2.4 ml |
| Antibiotics: | |
| Gentamicin | 50 µl |
| Fungizone | 50 µl |
| Caustic soda (1 M NaOH) | 100 µl |

The above components were mixed together, followed by cooling in ice.

Preparation of Umbilical Myofibroblast Suspension

Umbilical myofibroblasts were dispersed in a culture vessel using a solution of 0.1% trypsin and 0.1 mM EDTA to collect the cells. A part of the cells was taken and suspended in the DMEM medium (incl. 10% FBS) so as to be a concentration of $2 \times 10^6/11$ ml, followed by cooling in ice.

Preparation of a Collagen-Mixed Solution 6.6 ml of collagen solution (3 mg/ml, pH3.0) was added in the gel-adjusting solution, followed by being uniformly mixed together in a gentle manner. Umbilical myofibroblast suspension was added to the mixed solution, followed by being uniformly mixed together.

Preparation of Cultured Dermis

The collagen-mixed solution was poured into a rectangular culture vessel (85×125 mm) and then cultured for 2 to 5 hours at 37° C. in the presence of 5% $CO_2$ to solidify the solution. As a result, cultured dermis including umbilical myofibroblasts was prepared. A cross sectional view of such a tissue is shown in FIG. 2.

Example 8

Preparation of Cultured Skin using Umbilical Cells

Cultured dermis prepared in Example 7 was transferred to the upper portion of a two-layered culture vessel (Transwell, corstar) (ø24 mm), followed by inoculating $5 \times 10^4/cm^2$ of umbilical epithelium cells on the cultured dermis and culturing in MCDB153-1/4 (0.4% cx-FCS, 10% FCS) at 37° C. in the presence of $CO_2$ for about 10 days. Subsequently, only the dermis portion was dipped in the medium, while the epithelium portion was exposed to the air to culture for about 10 days. The epithelium was stratified to provide the cultured skin.

FIG. 3 shows a cross sectional view of such a tissue.

Effects of the Invention

According to this invention, constitutive cells of a umbilical cord can be recycled in a regenerative medicine and so on even though the umbilical cord is to be generally discarded from a mother or a baby after birth or after natural separation, with a few restrictions from a social ethical side and legal restrictions. Furthermore, the cells to be supplied are those of a fetal origin tissue obtained by a normal labor and are not an extra tissue being removed at the time of a surgical operation in connection with illness. There is a significant advantage in that normal fetal human cells without associated obvious lesions can be successively supplied in a stable manner.

What is claimed is:

1. A method of culturing umbilical cord epithelium cells, characterized by culturing in a medium umbilical cord epithelium cells separated from cells originated from tissue included in an umbilical cord, wherein the medium is a mixture of MCDB153 medium and DMEM medium in a volume ratio of 4:1 supplemented with epidermal growth factor, insulin, transferrin, hydrocortisone, ethanol amine, phosphoethanolamine and hypophysis extract.

* * * * *